United States Patent [19]

Wilkinson et al.

[11] Patent Number: 4,930,842
[45] Date of Patent: Jun. 5, 1990

[54] RESTRAINT CHAIR APPARATUS

[75] Inventors: Kerry E. Wilkinson; Larry A. DuVall, both of Phoenix, Ariz.

[73] Assignee: Parkway Manufacturing, Inc., Phoenix, Ariz.

[21] Appl. No.: 383,999

[22] Filed: Jul. 24, 1989

[51] Int. Cl.⁵ .............................................. A47C 31/00
[52] U.S. Cl. .................................... 297/466; 297/310; 297/DIG. 4
[58] Field of Search ......... 297/466, 464, 310, DIG. 4; 280/304.1, 250.1, 763.1

[56] References Cited

U.S. PATENT DOCUMENTS

| | | | |
|---|---|---|---|
| 2,670,669 | 3/1954 | Bauman | 280/763.1 |
| 3,256,040 | 6/1966 | Mize et al. | 297/310 |
| 4,647,066 | 3/1987 | Walton | 297/DIG. 4 |

FOREIGN PATENT DOCUMENTS

| | | | |
|---|---|---|---|
| 639715 | 4/1928 | France | 297/466 |
| 2102743 | 2/1983 | United Kingdom | 297/DIG. 4 |

Primary Examiner—Laurie K. Cranmer
Attorney, Agent, or Firm—H. Gordon Shields

[57] ABSTRACT

Restraint chair apparatus includes four legs, a padded seat, a relatively high padded back which extends a substantial distance above the top of the head of an individual being restrained in the chair, and foot rest on which the restrained person's feet are disposed. Restraint straps are used to secure the individual's legs, arms, waist, and chest to the chair. Pivoting outrigger elements may be utilized to prevent the chair apparatus from being tipped sideways. The chair may be movable on wheels so that a restrained individual may be transported in the chair.

23 Claims, 2 Drawing Sheets

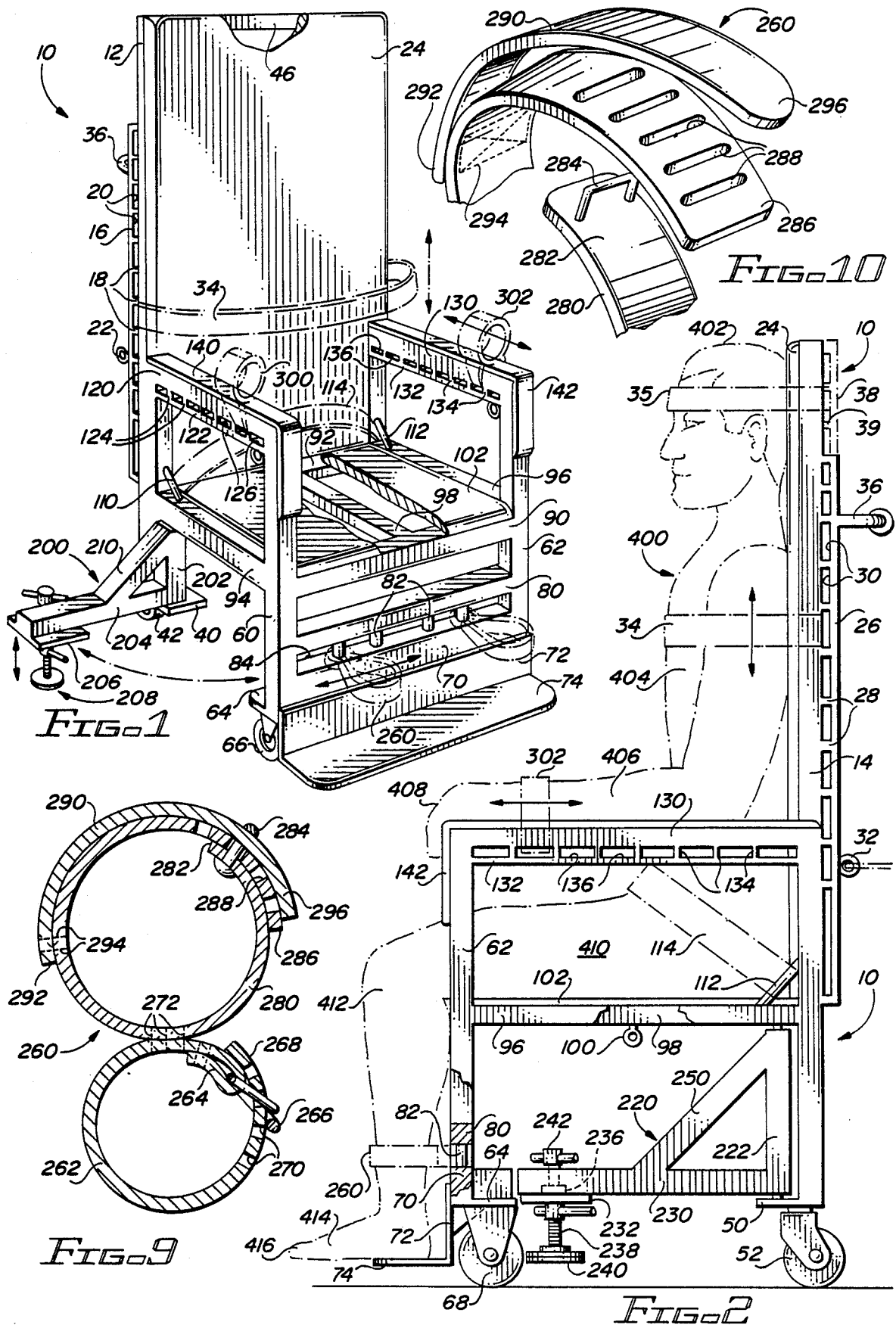

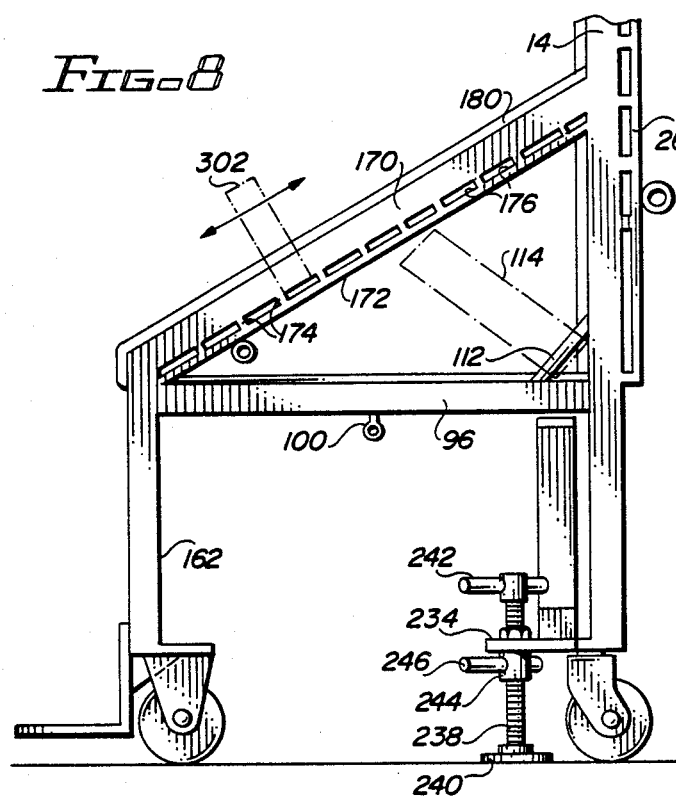
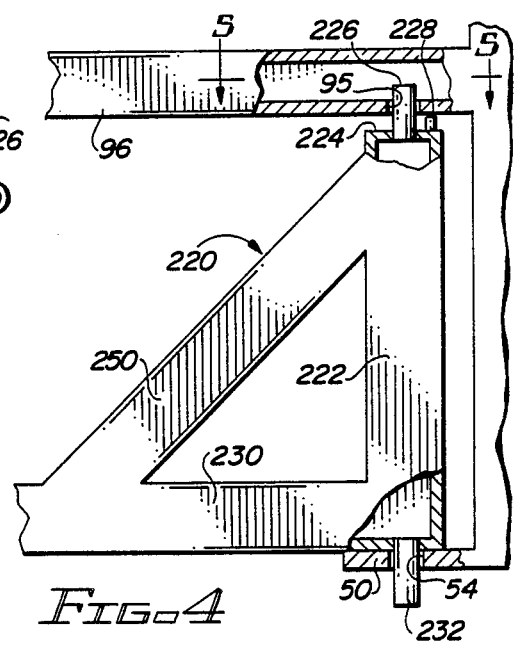
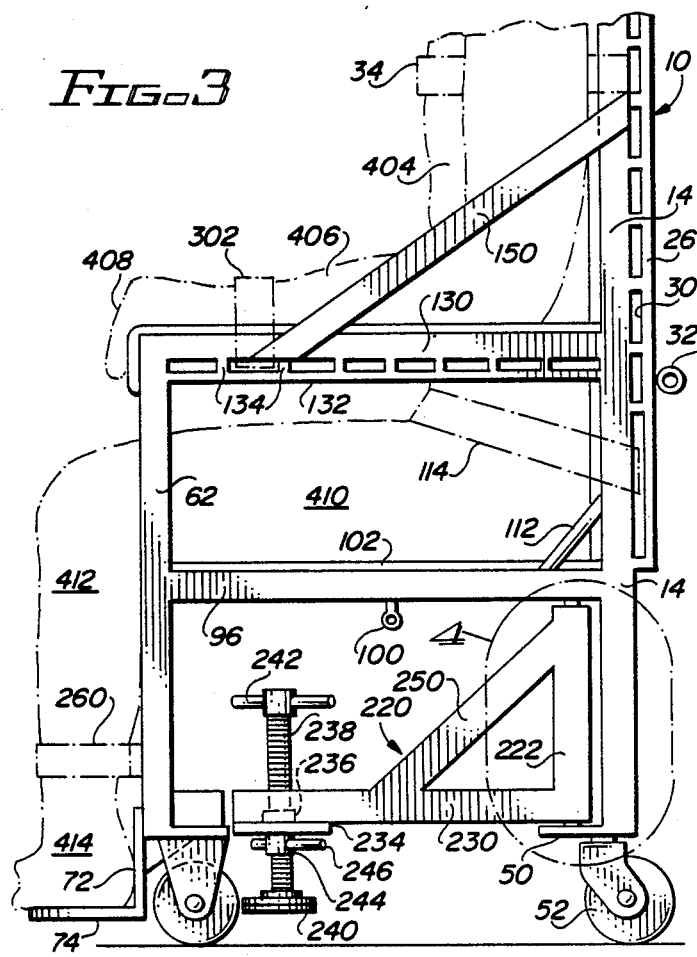
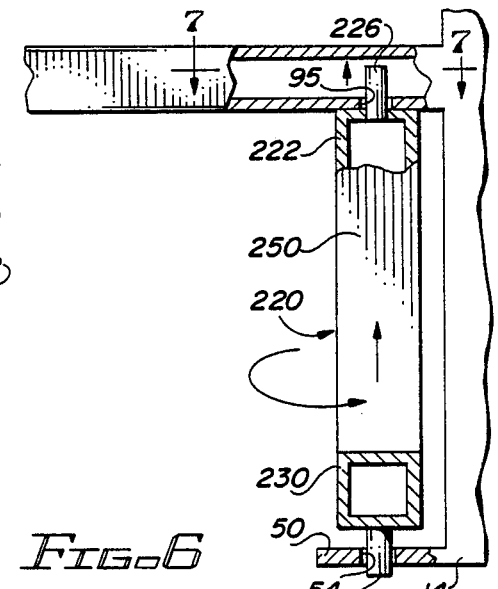
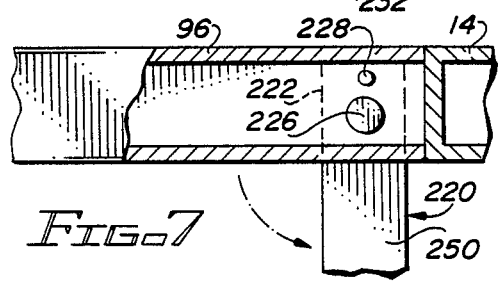

RESTRAINT CHAIR APPARATUS

BACKGROUND OF THE INVENTION

1. Field of the Invention:

This invention relates to chairs and, more particularly, to restraint chairs in which a person is restrained from movement.

2. Description of the Prior Art:

U.S. Pat. No. 575,941 (Baker) discloses a chair used for transporting prisoners. The apparatus is essentially a cage in the configuration of a chair. The apparatus includes wheels for moving the chair and a prisoner therein.

In addition to the above-described chair which comprises a restraint chair, there are a number of patents that disclose different types of restraints used primarily on wheelchairs. The idea behind the restraints is that individuals in the chairs need to be held in place to keep them from falling out of the chair. These types of restraints generally pertain to geriatric (elderly) patients and the like.

U.S. Pat. No. 2,707,988 (Shaub et al) discloses an infant sack used to restrain infants in strollers or similar type vehicles.

U.S. Pat. No. 3,669,107 (Posey) discloses a lap cover restraint for a patient in a wheelchair. The apparatus includes a bag-like element into which the patient is inserted. The bag-like element extends above the patient's waist. A strap extends from the bag over the patient's shoulders and is secured to the back of the chair.

U.S. Pat. No. 3,730,590 (Harris) discloses a chair designed particularly to support a patient in a shower. The chair includes a vertically extending portion to keep the patient's legs apart while the patient is being washed and dried.

U.S. Pat. No. 4,065,180 (Karay) discloses a chair which includes a leg restraining device to prevent the patient from sliding forward in the chair. The leg restraining device includes a cross panel secured to a pair of telescoping elements. The telescoping elements are secured to the sides of the chair and can be adjusted to fit any particular patient.

U.S. Pat. No. 4,170,991 (Kella) discloses a device for securing a patient to a wheelchair. The device comprises a harness system which fits the front of a patient, underneath a patient, and is secured to the back of the seat of the chair. The upper portion of the harness extends up over the chest of the patient and beneath the patient's arms to the back of the chair.

U.S. Pat. No. 4,113,307 (Day) discloses a travel chair, which appears to be a modified wheelchair designed particularly for transporting physically handicapped people. The chair includes a movable back with various strap elements for restraining a patient on a chair. The patient's legs, waist, and chest are appropriately secured to the chair while the patient is being transported.

U.S. Pat. No. 4,229,038 (Day) discloses a modification of the previously discussed '307 (Day) patent.

U.S. Pat. No. 4,807,937 (Harrigan) discloses a jump suit used for a patient and which in turn is used to secure a patient in a wheelchair. The jump suit restrains the individual by the manner in which the jump suit is secured to the chair.

In addition to the above-described patents, there are several patents which deal with restraining prisoners in vehicles. Such restraint elements typically include different types of straps or restraint elements that are secured to the vehicle while a prisoner is being transported.

U.S. Pat. No. 1,823,697 (Nenstiehl) discloses a handcuff system for restraining a prisoner in a vehicle. The apparatus includes a chain system secured to a spring for applying tension on the chain. Handcuffs are secured to the chain and to the prisoner being transported.

U.S. Pat. No. 4,004,583 (Johnson) discloses a strap restraint system for restraining a person in the front seat of a vehicle, next to the driver. The straps are secured outside the vehicle or by the door of the vehicle, to limit the movement of the prisoner being transported in the direction of the driver.

U.S. Pat. No. 4,728,553 (Daniels) discloses a restraint system in which a prisoner's legs are secured to the floor of the vehicle. The restraint system includes straps anchored to the floor of the vehicle. The strap extends around the prisoner's legs above the knees and the strap is in turn anchored to the floor.

The apparatus described above generally relate to some type of transportation and restraining a person, either a patient or a prisoner, while being transported. None of the devices is particularly effective or is designed to restrain a prisoner or a patient in a relatively immobile manner in order to prevent injury to the restrained individual or to others regardless of whether the restrained individual is being moved or is simply being held in a fixed location. Obviously, the wheelchair restraints are inapplicable to unruly prisoners, such as prisoners in an intoxicated state or in a drug-induced "high" state. The apparatus of the present invention is designed to restrain an individual in such state of intoxication or drug-induced "high" or in any other condition in which the individual may be a danger to themselves or to others.

SUMMARY OF THE INVENTION

The invention described and claimed herein comprises a chair having a foot rest, a seat, and a relatively high back with restraints for an individual's legs, arms, waist, and chest. The chair apparatus may include rollers for transporting the individual and pivotable outriggers for preventing the chair apparatus from being tipped over. The use of the foot rest and the relatively high back prevents a prisoner or person being restrained from being able to touch the floor and thus to obtain leverage to tip the chair over. The apparatus, including arm rests and the various straps, also restrains the individual by preventing excess movement of the head or upper torso that could also cause a chair to tip. Side to side tipping is prevented by the use of outriggers.

Among the objects of the present invention are the following:

To provide new and useful restraint chair apparatus;

To provide new and useful chair restraint apparatus securable to a floor;

To provide new and useful chair restraint apparatus attachable to a wall;

To provide new and useful chair apparatus for restraining an individual in the chair;

To provide new and useful chair apparatus movable from one location to another for transporting an individual in the chair;

To provide new and useful chair apparatus having outrigger elements to prevent the chair from being tipped;

To provide new and useful chair apparatus for restraining an individual while the individual is moved from one location to another; and To provide new and useful chair apparatus having restraints to prevent a person restrained in the chair from moving.

BRIEF DESCRIPTION OF THE DRAWING

FIG. 1 is a perspective view of the apparatus of the present invention.

FIG. 2 is a side view of the apparatus of FIG. 1.

FIG. 3 is a side view of a modification of the apparatus of FIGS. 1 and 2.

FIG. 4 is an enlarged view of a portion of the apparatus of the present invention.

FIG. 5 is a view in partial section taken generally along line 5—5 of FIG. 4.

FIG. 6 is an enlarged view sequentially illustrating the apparatus of FIGS. 4 and 5.

FIG. 7 is a view in partial section taken generally along line 7—7 of FIG. 6.

FIG. 8 is a side view of another alternate embodiment of the apparatus of the present invention.

FIG. 9 is a top view in partial section of an article usable with the apparatus of the present invention.

FIG. 10 is a perspective view of a portion of the apparatus of FIG. 9.

DESCRIPTION OF THE PREFERRED EMBODIMENT

FIG. 1 is a perspective view of restraint chair apparatus 10 of the present invention. FIG. 2 is a side view of the chair apparatus 10. FIG. 3 is a side view of the chair apparatus 10 of FIGS. 1 and 2 with an element added to the chair. For the following general discussion of the chair apparatus 10, reference will primarily be made to FIGS. 1, 2, and 3.

Restraint chair apparatus 10 includes a plurality of structural elements appropriately secured together, as by welding, to form a frame. The structural elements of the frame are preferably square steel tubing, although other structural materials may also be used. As indicated, the structural frame elements are preferably secured together by welding to provide a unitary chair structure.

At the rear of the chair apparatus 10 is a pair of vertical structural support elements, including a right rear vertical structural support element 12, and a left rear vertical structural support element 14. The vertical elements 12 and 14 are joined at their top by a top cross member 46. The lower portions of the elements 12 and 14 comprise the right and left rear legs, respectively, for the chair apparatus 10. The upper portions of the elements 12 and 14 comprise structural elements for the back of the chair apparatus 10.

Disposed behind the upper portions of the structural elements 12 and 14 is a pair of strap plates, including a right rear strap plate 14 and a left rear strap plate 26. The strap plates are separated from their vertical members by a plurality of divider elements 18. The plurality of divider elements 18 extends between the left rear vertical structural member 14 and the right rear strap plate 16. Between the dividers is a plurality of apertures 20.

The left rear strap plate 26 is secured to the left rear vertical structural member 14 by a plurality of divider elements 28. Between the divider elements is a plurality of apertures 30.

The purpose of the strap plates and the dividers, and the apertures, is to allow a chest strap 34, shown in dotted line, to extend through any of the apertures at any appropriate height for restraining an individual in the chair apparatus 10. The strap 34 is shown in phantom in FIGS. 1, 2, and 3.

As shown in FIG. 2, it may be desirable to increase the height of the rear structural members 12 and 14, and also the strap plates 16 and 26. Obviously, such vertical additions may easily be made and are shown in phantom in FIG. 2. FIG. 2 discloses a vertical extension 38 extending upwardly from the strap plate 26. A plurality of dividers 39 is also shown in FIG. 2. The dividers 39 are substantially identical to the dividers 28. The extension 38 is simply an upwardly extending addition of the element 26, or actually simply a longer element 26. The additional apertures 30, defined by the extension 38 and the dividers 39, allow for a head restraint strap 35, if so desired.

A similar upward extension of the strap 16, and of the dividers 18, would also be included to allow for the provision of the head restraint strap 35.

As indicated by the large double headed arrow in FIG. 2, the chest strap 34, and the head strap 35, may be positioned vertically as desired in accordance with the size of the individual restrained in the chair apparatus 10. The apparatus accordingly can accommodate persons of different sizes with the respective straps extending through the appropriate apertures for the most convenient fit. The apertures prevent the restraint straps from either moving upwardly or downwardly when the restraint straps are in place on the person being restrained in the chair apparatus 10.

If it is desired to locate the chair apparatus 10 in a specific location, and to secure the chair apparatus 10 to a wall, a pair of eye bolts 22 and 32 are appropriately secured, again as by welding, to the straps 16 and 26. The eye bolts may be secured to a wall by chains, straps, etc.

For maneuvering the chair apparatus 10, a handle 36 is provided. The handle 36 is simply a curved handle element, with appropriate padding if desired, appropriately secured, again as by welding, to the straps 16 and 26. The handle element 36 extends outwardly from the elements 16 and 26 a sufficient distance to allow a user to conveniently hold onto the handle 36 with hand and knuckle clearance, as is well known and understood.

At the bottom of the rear vertical frame members 12 and 14 are bottom plates. A bottom plate 40 is disposed at the lower end or bottom of the right frame member 12, and a bottom plate 50 is secured to the bottom of the left frame member 14. The plates 40 and 50 serve two functions. In the first place, rear caster wheels are secured to the plates, and in the second place, outrigger supports for stabilizing the chair apparatus 10 laterally are secured to the plates.

In FIG. 1, a right rear caster wheel 42 is shown secured to the plate 40, and in FIGS. 2 and 3, a left rear caster wheel 52 is shown secured to the plate 50.

In FIG. 1, an outrigger assembly 200 is shown extending outwardly from the plate 40, and in FIGS. 2 and 3 a left outrigger assembly 220 is shown secured to the plate 50. The outrigger assemblies 200 and 220 will be discussed in more detail below in conjunction with FIGS. 4, 5, 6, and 7.

The upper cross member 46 extends between the rear vertical elements 12 and 14. The cross member 46 comprises a top, generally horizontally extending, cross member. A back pad or cushion 24 is disposed against the upper portions of the members 12 and 14 and against the member 46. The pad or cushion 24 may be secured to the members 12, 14, and 46 in any appropriate manner. If desired, additional vertical or horizontal structural members may be included for strength and for supporting the pad 24.

The front of the chair apparatus 10 includes a pair of vertically extending front structural members or elements. The structural elements include a right front vertical leg element 60 and a left front vertical leg element 62. The lower portions of the vertical elements 60 and 62 comprise the front legs for the chair apparatus 10. The upper portions of the elements 60 and 62 comprise supports for arm rests, as will be discussed below.

Secured to the rear portions of, and extending between, the leg members 60 and 62 is a rear horizontally extending bottom plate 64. The bottom plate 64 preferably extends the full width of the chair apparatus 10. However, if desired, the plate may be divided into two smaller plates, similar to the plates 40 and 50. A right front wheel 66 and a left front wheel 68 are appropriately secured to the outer portions of the plate 64.

Extending between the lower portion of the legs 60 and 62 is a bottom cross member 70. Extending downwardly from the cross member 70 is a front vertical plate 72. Extending outwardly from the front vertical plate 72 is a front foot rest plate 74.

A mid front cross member 80 is disposed generally parallel to the lower front cross member 70 between the front legs 60 and 62. Extending between the cross members 70 and 80 is a plurality of vertical dividers 82. The vertical dividers 82 divide the space between the cross members 70 and 80 into a plurality of spaces 84. The purpose of the vertical dividers 82 is to allow foot or ankle restraints to be secured to them. A restraint 260 is shown in FIG. 9. The restraint 260 is shown in phantom in FIGS. 1, 2, and 3.

A front seat cross member 90 extends between the vertical front elements 60 and 62. A rear seat cross member 92 extends between the rear vertical elements 12 and 14. The seat cross members 90 and 92 are generally parallel to each other.

Extending between the front vertical member 60 and the rear vertical member 12 is a right side seat member 94. Extending between the front vertical member 62 and the rear vertical member 14 is a left side seat member 96. A center seat member 98 extends parallel to and between the members 94 and 96. The center seat member 96 extends between and is appropriately secured to the front cross member 90 and the rear cross member 92. A seat pad or cushion 102 is disposed on the various generally horizontally extending members 90, 92, 94, 96, and 98 to support a person. A similar pad or cushion 24 comprises a back cushion and is appropriately disposed against and secured to the members 12 and 14, 14, and 46. If desired, or if needed, there may be additional horizontally extending cross members extending between the vertical members 12 and 14 behind the cushion 24.

The horizontally extending seat members 90, 92, 94, 96, and 98 support the seat pad 102 and in turn are supported by the leg portions of the vertically extending front and rear elements 60, 62 and 12, 14, respectively.

Extending downwardly from the center seat member 98 is an eye bolt 100. The eye bolt 100 is appropriately secured to the seat member 98, as by welding. The purpose of the eye bolt 100 is to allow the chair apparatus 10 to be secured to the floor on which the chair apparatus 10 is disposed, as desired. Thus, in addition to, or instead of, securing the chair apparatus 100 to a wall by means of the eye bolts 22 and 32, the chair apparatus 10 may be secured to the floor by means of the eye bolt 100.

A diagonally extending lap belt anchor element 100 is appropriately secured to and extends between the rear vertical frame member 12 and the frame member 94. A similar lap belt anchor element 112 extends diagonally between, and is appropriately secured to, the vertical frame member 14 and the horizontal frame member 96.

A lap belt 114 is shown in phantom secured to the anchor elements 110 and 112 in FIGS. 1 and 2. In FIG. 3, the lap belt 114 is shown in phantom secured not to the anchor elements but extending through one of the apertures 30, a lower elongated aperture 30 between the frame element 14 and the strap plate 26. The lap belt 114 would, of course, also extend between a similar lower aperture 20 between the right side frame member 12 and the strap plate 16. Thus, the chair apparatus 10 allows for the flexibility of where a lap belt, a chest restraint strap, a head restraint strap, and leg or ankle restraint straps are secured so as to accommodate persons of various sizes, etc.

A generally horizontally extending right arm rest structural member 120 extends between the rear vertical frame member 12 and the upper portion of the front vertical leg 60. A strap plate 122 is disposed beneath the arm rest member 120 and is secured to the vertical elements 12 and 60. Between the strap 122 and the arm rest 120 is a plurality of dividers 124. There is a plurality of apertures 126 between the dividers 124.

A left arm rest structural member 130 extends between the top or upper portion of the front leg vertical frame member 62 and the left rear vertical frame member 14. A strap plate 132 is disposed beneath the frame member 120 and is attached to the vertical members 62 and 14. A plurality of dividers 134 extends between the frame member 130 and the strap 132, dividing the space between the members 132 and 134 into a plurality of apertures 136.

The apertures 126 and 136 allow for the placement of arm restraint straps 300 and 302, shown in phantom in FIGS. 1, 2, and 3, at many locations. The arm restraint straps 300 and 302 may be located anywhere along the arm rest structural members 120 and 130, as desired, depending upon the specific needs of the person being restrained in the chair apparatus 10, to secure the person's arms (including the wrists) to the chair.

On top of the arm rest 120, and extending downwardly onto the front of the vertical front member 60 is a pad 140. A similar pad 142 is disposed on the top of the horizontally extending arm rest frame member 130 and downwardly along the front of the vertically extending front frame member 62.

For the convenience and comfort of the individual disposed and restrained in the chair apparatus 10, the pads 24, 102, 140, and 142, are appropriately disposed on and secured to the chair apparatus in well known and understood manners. The pads provide not only comfort for the person being restrained in the chair apparatus 10, but also prevent possible injury to the individual in case of attempted violent movements, or inadvertent movements, as may happen with certain kinds of patients, prisoners, etc.

In FIG. 3, a diagonally extending arm brace 150 is shown extending between the rear vertical frame member 14 and the horizontally extending arm rest frame member 130. The purpose of the diagonally extending arm brace element 150 is to prevent a person being restrained in the chair apparatus 10 from moving the elbow outwardly to increase the leverage or the ability of the arm to make violent maneuvers which may cause structural damage to the chair apparatus, and particularly to the arm rest elements 130 and the front vertical legs or frame members, such as the leg member 62 shown in FIG. 3. Obviously, there is a similar and parallel diagonally extending frame member on the opposite side of the chair, appropriately secured to and between the right rear vertical frame member 12 and the horizontally extending arm rest frame member 120.

FIG. 4 is an enlarged view in partial section of a portion of the chair apparatus 10, illustrating the construction of the outrigger 220. FIG. 4 is taken generally from oval 4 of FIG. 3. FIG. 5 is a view in partial section taken generally along line 5—5 of FIG. 4, illustrating details of the operation of the outrigger 220. FIG. 6 is a view in partial section sequentially following FIG. 4, illustrating the operation of the outrigger 220. FIG. 7 is a view in partial section taken generally along line 7—7 of FIG. 6, illustrating details of the construction and operation of the outrigger 220. For the following discussion of the outrigger 220, reference will primarily be made to FIGS. 2, 3, 4, 5, 6, and 7. In addition, for comments regarding the outrigger, reference will be made to FIG. 1.

Referring particularly to FIG. 1, the outrigger 200, which is the right outrigger, includes a vertical member 202. The member 202 extends between the plate 40 and the frame member 94. The vertical member 202 is secured to a base member 204. The member 204 extends substantially perpendicularly to the vertical member 202. The base member 204 extends generally horizontally. The base member 202 and the base member 204 are appropriately secured together, as by welding. At the outer end of the base member 204 is a plate 206. A floor lock assembly 208 is secured to the plate 206.

A diagonal frame member 210 extends between the upper portion of the vertical frame member 202 and the horizontal or base member 204. The diagonal member 204 extends to the base member 204 at about the mid point of the base member 204.

As illustrated by the double headed arrow in FIG. 1, the outrigger 200 moves in an arc between its closed or nested position and an open, use, position. In the closed position, the members 202, 204, and 210 are aligned with a plane defined by the members 12, 60, 94. In the outer or use position, the frame members 202, 204, and 210 are disposed generally perpendicular to the plane defined by the members 12, 60, and 94.

The left outrigger 220 is substantially identical to the right outrigger 200. The left outrigger 220 is shown in greater detail than the right outrigger 200. The extra detail is shown in FIGS. 4, 5, 6, and 7. It will be understood that the detailed elements illustrated in FIGS. 4, 5, 6, and 7, and discussed herein, are also found in the right outrigger 200. For the following discussion, reference will primarily be made to FIGS. 4, 5, 6, and 7, but reference will additionally be made to FIGS. 2 and 3, for the following discussion of the outrigger 220.

The outrigger 220 includes a vertical member 222, which is preferably square tubing. At the top of the square tubing vertical member 222 is an end cap or plate 224. A top or upper pivot shaft 226 extends upwardly from the end cap or plate 224. The pivot shaft 226 extends into a hole or aperture 95 in the bottom web of the left side seat member 96. In addition, a locking pin 228 also extends upwardly from the plate 224. The bottom web of the frame member 96 includes an aperture or hole 97 which receives the pin 228, as will be discussed in more detail below.

Extending outwardly from, and secured to, the vertical member 222 is a base member or lower horizontally extending member 230. Extending downwardly from the base member 230 is a bottom or lower pivot shaft 232. The pivot shaft 232 is appropriately aligned with the pivot shaft 226. The bottom pivot shaft 232 similarly extends through a hole or aperture 54 in the bottom plate 50. The hole 54 is, of course, aligned with the hole 95 in the structural member 96. This is best shown in FIGS. 4 and 6. The outrigger 220 pivots on the pins 226 and 232 into and out of position on the basic frame of the chair apparatus 10.

At the outer end of the base member 230 is a plate 234. A floor lock assembly is secured to and movable relative to the plate 234. The floor lock assembly includes a nut 236 appropriately welded to the plate 234. This is shown in FIGS. 2 and 3. In the alternative, an aperture extending through the plate 234 may be threaded to receive a threaded rod 238. The threaded rod 238 extends through the nut 236, if such is used, and also through an aperture in the plate 234 about which the nut 236 is disposed. Whether or not the aperture in the plate 234 is threaded depends, of course, on the presence of the nut 236. Or, phrased another way, the presence of the nut 236 depends on whether or not the aperture or hole in the plate 234 is threaded to receive the threaded rod 238.

At the bottom of the threaded rod 238 is a base or foot 240. The base or foot 240 preferably includes a non slip pad, such as rubber, on its bottom. The presence of non slip pads will aid in stabilizing the chair apparatus 10 when the outriggers 200 and 220 are deployed or moved outwardly from the basic chair frame.

At the top of the threaded rod 238 is a handle rod 242. Rotation of the handle rod 242 causes the threaded rod 238 to move vertically upwardly or downwardly, according to the direction of rotation, of course. Once the outrigger 240 is deployed outwardly from the chair, the threaded rod 238 is rotated downwardly by the handle 242 until the base or foot 240 makes contact with the floor. In a similar manner, the floor lock assembly 208 is actuated when the assembly 200 is moved outwardly to provide the lateral stability for the chair apparatus 10.

When the outrigger 220 has been moved outwardly or deployed for stability purposes, and the base or foot 240 is in contact with the floor on which the apparatus is disposed, a lock nut 244 secures the rod 238 in place. The lock nut 244 is disposed on the threaded rod beneath the plate 234 and is moved by a handle 246. The lock nut 244 is moved by the handle 246 upwardly until the nut 244 is disposed against the plate 234 to secure the rod 238, and accordingly the base or foot 240, in place. Again, the corresponding elements of the floor lock 208 are similarly appropriately moved to provide the locking of the outrigger 200 in place.

Referring particularly to FIGS. 4 and 5, it will be noted that as the outrigger 220 pivots outwardly, the pin 228 (see FIG. 4) will move through an arc of about ninety degrees so that the pin 228 will be aligned with the hole 97 (see FIG. 5).

As the screw 238 is moved downwardly and as the pad 240 contacts the floor, continued rotation of the rod 238 will cause the vertical frame member 222, and of course the horizontal frame member 230, to move upwardly. The upward movement will cause the pin 228 to extend into the hole 97, thus locking the outrigger 220 or fixing the outrigger 220 in position relative to the frame member 96, and the other fixed frame elements or members of the chair apparatus 10.

At such time as the top plate 224 contacts the bottom of the frame member 96, the lock nut 244 may be moved upwardly against the plate 234. The contact between plate 224 and the frame member 96 will be easily detected simply by the increase of force required to continue the rotation of the screw 238. Moreover, a simple glancing or visual observation of the outrigger 220 relative to the frame 96 will let the observer of the chair apparatus 10 know when the outrigger 220 is sufficiently stabilized to engage the lock nut 244.

As indicated before, the outrigger 200 is substantially identical in structure and in operation to the outrigger 220.

Referring to FIGS. 6 and 7, the outrigger 220 is shown disposed against the frame member 96. In FIG. 7, the pin 228 is shown extending in the hole 97, locking the outrigger 220 in position relative to the frame member 96 and to the other fixed frame members.

Referring now specifically to FIGS. 4 and 6, it will be noted that the overall length of the bottom pivot pin 232 is sufficient to allow for the full movement of the outrigger 220 upwardly to the position shown in FIG. 6 without having the bottom pivot pin 232 clear its aperture 54 in the plate 50. Similarly, as shown in FIG. 4, the height of the upper pivot pin 226 is sufficient to allow the outrigger 220 to maintain its pivoting relationship without coming loose or coming out from its hole 95 in the frame member 96. And, as shown in FIG. 4, the height of the pin 228 is such that the pin 228 does not interfere with the pivoting of the outrigger 220. Rather, there is sufficient clearance between the top of the pin 228 and the bottom of the frame member 96 to allow the outrigger 220 to pivot without interference.

A diagonal brace 250 extends between the upper portion of the vertical member 222 and the horizontal member 230. The diagonal brace 250 extends to about the mid point of the horizontal base member 230.

While not shown, the outriggers 200 and 220 may be secured against the main chair frame by means of magnetic elements, or the like. The presence of such magnetic elements will help to hold the outriggers in place against the chair frame while the chair apparatus 10 is moved from place to place. Of course, once in place, in either a fastened position utilizing the eye bolts 22, 32 or the eye bolt 100, or otherwise, the outriggers 200 and 220 may be deployed outwardly for lateral stability and locked in place.

FIG. 8 is a side view of an alternate embodiment of the chair apparatus 10. The chair apparatus 10 is substantially as described above with the exception of the front leg members and the arm rest members. In the embodiment of FIG. 8, the front leg members are shortened. For example, a front left leg member 162 is illustrated in FIG. 8 as extending only about to the upper portion of the side seat frame member 96, or slightly above it. In place of the generally horizontally extending arm rest member 130 of FIGS. 1, 2, and 3, an arm rest member 170 is shown in FIG. 8 extending diagonally from the vertical rear frame member 14 downwardly to the top or upper portion of the left front leg frame member 162.

Beneath the diagonally extending arm rest member 170 is a strap plate 172. A plurality of dividers 174 extend between the strap plate 172 and the arm rest member 170. A plurality of apertures 176 is defined between the dividers 174 and the plate 172 and arm rest member 170. The arm or rest restraint strap 302 may extend through any of the apertures 176.

An appropriate pad 180 is disposed on the diagonally extending member 170 and downwardly along the front portion of the front left leg member 162.

The purpose of the diagonally extending arm rest member 170 is to limit to a substantial extent or degree the amount of leverage which a person restrained in the chair is able to exert against the frame member 170 and the other frame members to which the member 170 is secured. With the person's arm being restrained in the chair generally straight out, substantially less leverage may be exerted by the arm so disposed than when the arm is bent at the elbow at substantially a right angle. Accordingly, a person restrained with the arms generally straight out, that is, with the elbow not bent, is less likely to either break the chair or cause injury to the restrained individual.

FIGS. 9 and 10 illustrate restraint straps or belts typically used to restrain the legs or ankles and the arms or wrists of individuals. In FIG. 9, the restraint strap 260 is shown as including two different straps, a base strap 262 and a fastening strap 280. The base strap 262 is appropriately secured, in case of leg restraints, to one of the vertical dividers 82. In the case of wrist or arm restraints, the base strap 262 extends about an arm rest and through the holes or apertures 126, 136, 176.

At one end of the base strap 262 is a loop 264. Disposed within the loop 264 is a buckle 266. The loop 264 is preferably stitched together after the buckle 266 is disposed in the loop. At the opposite end of the strap 262 from the loop 264 is a free end 268. Extending rearwardly from the free end 268 is a plurality of spaced apart and aligned holes 270. The holes 270 cooperate with the buckle to secure the base strap to the chair apparatus 10.

The fastening strap 280 is secured to the base strap 262 by appropriate stitching 272. The fastening strap 280 includes an end 282 and an end 296. At the end 282 a loop 284 extends upwardly. The loop 284 is a metal loop, anchored to the end 282. See FIG. 10. The opposite or free end 286 of the fastening strap 280 includes a plurality of generally parallel and spaced apart openings 288 extending rearwardly from the end 286. The openings 288 are large enough to receive the loop 284. The fastening strap 280 is placed around an individual's leg or ankle or arm or wrist until the strap 280 is fairly snug. At the point of snugness, the closest opening 288, as appropriate, is disposed onto the loop 284 such that the loop 284 extends through an opening 288 and upwardly from or above the strap 280. A locking strap 290 then extends through the loop 284 to secure the strap 280 to the individual being restrained.

The locking strap 290 includes a fixed or stitched end 292 and a free end 296. The free end 296 extends outwardly to, or slightly beyond, the end 286. The locking strap 290 is appropriately secured, as by stitching 294, to the fastening strap 280. The locking strap 290 is narrower than the fastening strap 280, and is generally about the width of the loop 284 so that when the free end 296 extends through the loop 284, the fastening strap is relatively snugly in place.

It will be understood that with the employment of the restraint strap 260, with the fastening strap 280 secured thereto, a person restrained in the chair has only limited movement. Obviously, the fastening strap should not be so tight as to cause circulatory problems, but it should be sufficiently tight to adequately restrain the individual.

Referring again particularly to FIGS. 2 and 3, there is shown in phantom a person disposed in the restraint chair apparatus 10. The person 400 includes a head 402, a chest or torso 404, a left forearm 406, and left hand 408, a left thigh 410, a left lower leg 412, a left ankle 414, and a left foot 416. While the person 400 is profiled only from the left, it is obvious that the person 400 includes the corresponding right arm, leg, and foot elements, etc. Insofar as the restraint chair apparatus 10 is concerned, the person 400 is seated in the chair and is restrained therein.

The head restraint strap 35 is shown in phantom disposed about the head 402 of the person 400. The strap 35 extends about the upper portion of the vertical frame members 12 and 14 and through upper holes or apertures between the frame members and the strap plates, as discussed above.

A chest strap 34 is disposed about the upper portion of the torso 404. The strap 34 extends through the holes or apertures 20 and 30 (see also FIG. 1) between the respective vertical frame members and the strap plates.

A wrist or forearm restraint 302 is shown about the wrist or lower forearm 406, adjacent to the hand 408. The ankle strap 260 is shown about the lower leg, or about slightly above the ankle 414 of the person 400.

It will be noted that the left foot 416 is disposed on the foot rest plate 74. With both feet on the foot rest plate 74, the person 400 is entirely confined to the chair apparatus 10. Accordingly, the person 400 will not be able to obtain any leverage from the floor in order to try to tip the chair apparatus in any manner. Moreover, with the outriggers 200 and 220 moved outwardly, the chair apparatus 10 is braced against side to side movements.

Since the person 400 is substantially completely restrained, any movement of the individual or person 400 is quite limited. The limitations are such that substantially no large movements are possible by any part of the body. Accordingly, movement of the chair 10, even with the outriggers not deployed, and even with no fastening elements between the chair 10 and the wall or floor, is highly unlikely. Furthermore, by the manner in which the restraint straps are applied to the individual, damage to the chair, even by a large, very muscular individual, is highly unlikely. With a diagonal strap, such as the strap 150 of FIG. 3, even a large muscular person will not be able to flex or to move arms outwardly sufficiently to obtain leverage to do any physical harm to the arm rest, or the like. In the alternative, the slanting arm rest, such as the arm rest 170 in FIG. 8, even prevents the flexing in any substantial manner by the arm of the individual. In other words, arm movements or arm flexing of an individual restrained in the chair apparatus 10 may be substantially completely eliminated.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Restraint chair apparatus comprising, in combination:
    frame means for supporting a person being restrained, including
        seat means on which the person being restrained sits,
        leg means, including rear leg means and front leg means, for supporting the seat means,
        back means extending upwardly from the rear leg means and against which the person being restrained is disposed, and
        arm rest means secured to the back means and front leg means for supporting the arms of the person being restrained;
    outrigger means secured to the frame means for providing lateral support for the frame means; and
    restraint means for securing the person being restrained to the frame means, including chest restraint means, lap restraint means, arm restraint means, and leg restraint means.

2. The apparatus of claim 1 in which the chest restraint means includes
    a first strap plate secured to and spaced apart from the back means,
    a first plurality of divider elements extending between the first strap plate and the back means and defining therewith a first plurality of apertures, and
    chest strap means extending through one of the plurality of apertures and about the chest of the person being restrained.

3. The apparatus of claim 1 in which the arm restraint means includes
    a second strap plate spaced apart from and secured to the arm rest means,
    a second plurality of divider elements extending between and secured to the arm rest means and to the second strap plate and defining therewith a second plurality of apertures, and
    arm strap means extending through one of the second plurality of apertures and about an arm of the person being restrained.

4. The apparatus of claim 1 in which the arm restraint means includes strap means extending diagonally between the back means and the arm rest means for preventing the outward flexing of the arms of the person being restrained.

5. The apparatus of claim 1 in which the lap restraint means includes a lap restraint belt secured to frame means.

6. The apparatus of claim 5 in which the frame means further includes first and second anchor pins extending between the back means and the seat means, and the lap restraint belt is secured to the first and second anchor pins.

7. The apparatus of claim 1 in which the frame means further includes foot rest means secured to the front leg means on which the feet of the person being restrained are disposed.

8. The apparatus of claim 7 in which the restraint means includes leg restraint means for securing the person's feet to the foot rest means.

9. The apparatus of claim 8 in which the front leg means includes a right front leg and a left front leg spaced apart from each other and a front cross member extending between and secured to the right and left front legs, and the leg restraint means include
   a plurality of divider elements extending between and secured to the front cross member and the foot rest means, and
   leg strap means secured to any of the plurality of dividers to secure the person's leg to the frame means and to the foot rest means.

10. The apparatus of claim 1 in which the arm rest means includes a first element extending outwardly from the back means generally horizontally and a second element extending downwardly from the first element remote from the back means and to the front leg means.

11. The apparatus of claim 10 in which the arm rest means further includes a third element extending generally diagonally between the back means and the first element for preventing the outward flexing of an arm of the person being restrained.

12. The apparatus of claim 1 in which the arm rest means includes an arm rest member extending generally diagonally between the back means and the front leg means and on which the arm of the person being restrained is disposed.

13. The apparatus of claim 1 in which the outrigger means includes a first outrigger secured to the frame means and movable between a stored position adjacent to the frame means and a user position away from the frame means.

14. The apparatus of claim 13 in which the outrigger means further includes a second outrigger secured to the frame means remote from the first outrigger means and movable between a stored position adjacent to the frame means and a user position away from the frame means.

15. The apparatus of claim 14 in which the first and second outriggers each include floor lock means for stabilizing the outriggers in their use position.

16. The apparatus of claim 15 in which the floor lock means includes a foot member movable between a down position to stabilize an outrigger in its use position and an up position to allow the outrigger to move to its stored position.

17. The apparatus of claim 1 in which the frame means further includes means for securing the chair apparatus to a wall.

18. The apparatus of claim 1 in which the frame means further includes means for securing the chair apparatus to a floor on which the chair apparatus is disposed.

19. The apparatus of claim 1 in which the leg means includes wheel means for moving the chair apparatus from one location to another location.

20. Restraint chair apparatus comprising, in combination:
   frame means for supporting a person being restrained, including
      seat means on which the person being restrained sits,
      leg means, including rear leg means and front leg means, for supporting the seat means,
      back means extending upwardly from the rear leg means and against which the person being restrained is disposed, and
      arm rest means secured to the back means and front leg means for supporting the arms of the person being restrained;
   outrigger means pivotally secured to the frame means and movable from a stored position at the frame means to a use position away from the frame means for providing lateral support for the frame means; and
   restraint means for securing the person being restrained to the frame means.

21. The apparatus of claim 20 in which the outrigger means includes first and second outriggers, and the first outrigger pivots in a first direction to its use position and the second outrigger pivots in a second direction to its use position.

22. The apparatus of claim 20 in which the outrigger means includes adjustable floor lock means for stabilizing the outrigger means in the use position.

23. The apparatus of claim 22 in which the adjustable floor lock means includes a foot member movable between an up position for storing the outrigger means and a down position for stabilizing the chair apparatus in the use position of outrigger means.

* * * * *